United States Patent [19]
Bellet et al.

[11] Patent Number: 5,763,724
[45] Date of Patent: Jun. 9, 1998

[54] METHOD OF MANUFACTURING CHEMICAL PRODUCTS

[75] Inventors: Serge Bellet, Chateauneuf Les Martigues; Marc Loublier, Sausset Les Pins; Guy Margail, Martigues, all of France

[73] Assignee: Naphtachimie S.A., Courbevoie, France

[21] Appl. No.: 463,032

[22] Filed: Jun. 5, 1995

Related U.S. Application Data

[63] Continuation of Ser. No. 242,040, May 12, 1994, abandoned, which is a continuation of Ser. No. 927,629, filed as PCT/FR91/01074, Dec. 26, 1991, abandoned.

[30] Foreign Application Priority Data

Dec. 28, 1990 [FR] France ............................ 90 16627

[51] Int. Cl.$^6$ .............................. C07C 4/02; C07C 5/327
[52] U.S. Cl. ........................ 585/648; 585/653; 585/654; 585/752; 585/927
[58] Field of Search .......................... 585/648, 652, 585/653, 752, 921, 654, 655; 422/209

[56] References Cited

U.S. PATENT DOCUMENTS

| | | |
|---|---|---|
| 3,183,967 | 5/1965 | Metenleiter . |
| 3,819,740 | 6/1974 | Hori .................................... 360/679 |
| 4,271,007 | 6/1981 | Souhrada et al. .................. 208/48 R |
| 4,368,677 | 1/1983 | Kline . |
| 4,827,074 | 5/1989 | Sueva et al. ........................ 585/648 |

FOREIGN PATENT DOCUMENTS

| | | |
|---|---|---|
| 2221426 | 10/1974 | France . |
| 2600665 | 12/1987 | France . |

*Primary Examiner*—Ponnathapura Achutamurthy
*Attorney, Agent, or Firm*—Ladas & Parry

[57] ABSTRACT

The present invention relates to a method of manufacturing one or more chemical products in which a chemical reaction is performed by causing one or more reagents to flow along the inside of a tube disposed in a radiation zone of a furnace. In the method, at least a portion of the tube is caused to vibrate so as to limit the deposition of reaction by-products on the inside wall of the tube. More particularly, the tube can be vibrated at a frequency lying in the range 50 Hz to 2000 Hz. The invention also provides apparatus for performing the method of the invention, which apparatus comprises a furnace including a radiation thermal enclosure through which at least one tube passes, which tube is provided with at least one excitation means suitable for generating tube vibration.

28 Claims, 1 Drawing Sheet

METHOD OF MANUFACTURING CHEMICAL PRODUCTS

This is a continuation of application Ser. No. 08/242,040 filed on May 12, 1994, abandoned, which is a continuation of application Ser. No. 07/927,629 filed Oct. 13, 1992 (now abandoned) and International Application PCT/FR91/01074 filed on Dec. 16, 1991, and which designated the U.S.

FIELD OF THE INVENTION

The present invention relates to a method of manufacturing one or more chemical products including a chemical reaction that is performed inside a tube. The present invention also provides apparatus constituted by a furnace for implementing the method.

DESCRIPTION OF RELATED ART

It is known that chemical reactions can be performed at high temperature by methods that consist in causing the reagents to flow along a tube maintained at high temperature and disposed inside a radiation zone of a furnace. More particularly, for manufacturing olefins, in particular ethylene, propylene, or isobutene, it is known that a steam cracking reaction of liquid or gaseous hydrocarbons can be performed in furnaces having an outlet temperature generally lying in the range 750° C. to 880° C. In that method known as "steam pyrolysis" or "steam cracking", a mixture of hydrocarbons and steam flows along a cracking tube so disposed in the form of a coil in a furnace as to pass through a radiation zone of the furnace. All of these chemical reactions are usually performed in modern furnaces that generally comprise a heater device constituted by burners disposed on the baseplate and/or on the inside walls of the furnace. The thermal heating power of the burners is advantageously distributed along the tube so that the reagents of the reactions are subjected to a temperature that increases along the tube from a temperature at the inlet to the radiation zone to a temperature at the outlet from said zone.

When the tube is maintained at high temperature, it is important to monitor accurately the temperature of its outside surface, referred to as the "skin temperature". Given the thermal stresses on the tube and given that it is generally desirable to avoid premature aging of the tube, the thermal heating power of the burners is adjusted so that the skin temperature as measured at any point on the tube is always less than a limiting skin temperature.

The limiting skin temperature is a technical characteristic of the tube and depends greatly on the desired lifetime for the tube and on the nature of the metal or the alloy from which the tube is made. When hydrocarbons are being subjected to a steam cracking reaction, the limiting skin temperature generally lies in the range 1050° C. to 1110° C.

Most chemical reactions performed in a tube suffer from the major drawback of generating by-products that are deposited on the inside wall of the tube. Thus, while performing steam cracking on hydrocarbons, there is observed, particularly when the cracking temperature is high and/or when the cracking tube is fed at a high rate, the formation of a layer of coke on the inside of the cracking tube, and this occurs in spite of the normally turbulent flow of the mixture of hydrocarbons and steam. Deposits of by-products are particularly troublesome since they significantly limit the transfer of heat through the wall of the tube. Thus, in order to maintain a constant reaction temperature, it is observed that it is necessary to increase the heating power delivered by the burners as the thickness of the layer of by-products increases, thereby increasing the energy consumed by the furnace. In addition, because of the increase in the heat power delivered by the burners, the skin temperature of the tube is observed to increase.

This phenomenon is particularly detrimental since the more the deposits of by-products increase, the more difficult or even impossible it becomes to keep to a skin temperature below the limiting skin temperature, if it is desired to perform the reaction with yield and efficiency that are sufficient. Under such conditions, it is necessary to stop the reaction on a regular basis in order to remove the deposits of by-products. In the particular case of a steam cracking reaction, such removal is performed by a decoking operation on the cracking tube. This operation consists in causing a mixture of air and steam to flow inside the cracking tube while the tube is kept at a temperature that is high enough to make it possible to burn off and remove all of the coke that is present. In practice, it is observed that a decoking operation takes a relatively long period of time, with the total time required being close to 24 hours, and that it is nevertheless desirable to decoke a tube at a high frequency, usually close to once every two or three months.

Given that the chemical reactions are generally performed in installations of large size, the stops required for removing the layers of by-products from the inside of a tube give rise to a significant loss of production. Thus, numerous studies have been performed over the years both on a laboratory scale and on an industrial scale for the purpose of finding a method that makes it possible to limit the deposition of by-products on the inside wall of the tube.

A method is known from U.S. Pat. No. 4,368,677 enabling the deposition of the by-products from a combustion reaction to be prevented on the outside wall of a heat exchanger tube disposed in a boiler with water flowing inside the tube. According to that method, a plurality of pulsed gas flows are used which deliver into the boiler, a hot gas, heat, and soundwaves. In particular, a first pulsed gas flow is used to produce a fuel constituted by particles of uniform size. In addition, a second gas flow is directed against the outside wall of the heat exchanger, and preferably parallel to the tubes constituting the heat exchanger, so as to avoid vibration thereof. Consequently, that method cannot be used to limit the deposition of by-products on the inside wall of a tube in which a chemical reaction is being performed.

SUMMARY OF THE INVENTION

A method of manufacture has now been found that enables a chemical reaction to be performed inside a tube disposed in the radiation enclosure of a furnace while avoiding the abovementioned drawbacks. In particular, it enables the deposition of by-products on the inside wall of the tube to be limited, sufficiently to avoid the need to stop the chemical reaction and without changing its efficiency and/or its yield. In addition, the method of the invention can easily be adapted to industrial installations that are already in existence.

Firstly, the present invention provides a method of manufacturing one or more chemical products in which a chemical reaction is performed by causing one or more reagents to flow inside a tube disposed in a radiation zone of a furnace, wherein vibrations are applied to at least a portion of the exterior of the tube to an extent to limit the deposition of reaction by-products on the inside wall of the tube. For this purpose the tube is usually vibrated at a frequency lying in the range 50 Hz to 2000 Hz, and preferably lying in the range 100 Hz to 1000 Hz.

In addition, the best results are obtained the tube is caused of vibrate transversely of its longitudinal axis. The transverse vibration of the tube can be such that at least one point of the tube vibrates with an amplitude (i.e. the displacement of said point between its two extreme positions) greater than $10^{-6}$ and preferably greater than $10^{-4}$ times the inside diameter of the tube. However, it is preferable for the vibration amplitude of all of the points of the tube to be not too great in order to avoid premature reduction in the mechanical properties of the tube which could give rise to the tube breaking or to its fixings breaking. In addition, the transverse vibration of the tube can be performed at substantially a resonant frequency of the tube as disposed in the radiation zone of a furnace. Under such circumstances, the transverse vibration of the tube is characterized by deformation that includes vibration nodes at which the displacement amplitude is zero and vibration antinodes at which the amplitude is at a maximum. The positions of the nodes and of the antinodes can be changed several times during the method by selecting vibration at different resonant frequencies.

In the method of the invention, the deposition of by-products on the inside wall of the tube can partially or totally avoid by-products being deposited or can partially or totally eliminate deposits that already exist so as at least partially to remove such reaction by-products. The tube can be vibrated at isolated moments in time or intermitently. Under such circumstances, the method is adapted more to eliminating existing deposits. The tube can also be vibrated continuously, in which case the method is adapted more to avoiding deposition.

The tube can be caused to vibrate by any means. In particular, it can be caused to vibrate by a source of mechanical vibrations. In addition, given that the radiation zone generally does not operate in a vacuum, and that it therefore contains a mixture of gases, the tube can also be caused to vibrate by a pressure wave outside the tube. The wave can propagate in any direction. In particular, it can propagate in a direction perpendicular or substantially perpendicular to the tube. Furthermore, the pressure wave can be a standing pressure wave established outside the tube in the radiation zone. The standing wave is characterized by the fact that pressure nodes and antinodes are formed in the radiation zone having positions that depend on the wavelength of the standing wave. Advantageously, when the direction of the standing wave is perpendicular to the direction of the tube, a wavelength is selected such that a pressure antinode lies in the vicinity of the tube, thereby significantly increasing the efficiency of the method.

Given that the radiation enclosure of the furnace is provided with burners, the gas mixture contained in said enclosure comes, in part, from the combustion gases from the various burners. With certain dispositions of the burners on the walls of the radiation enclosure and/or with certain compositions of the fuel feeding the burners, the invention also provides for the vibrations of the flames of said burners generating pressure waves to be sufficient for vibrating the tube so as to limit the deposition of by-products.

The present invention is based on the surprising discovery that vibration of the tube makes it possible to considerably limit the deposition of by-products on its inside wall without otherwise changing the conditions of the chemical reaction, and in particular its efficiency. Surprisingly, it has also been observed that the tube can be vibrated with practically no premature aging thereof, and in particular with practically no premature reduction in its mechanical properties. The advantage of the method lies essentially in a major reduction in the frequency at which operations need to be performed to eliminate deposits of by-products using means other than those implemented in the method of the invention.

By virtue of the method of the invention, any chemical reaction normally performed in a tube can be performed. The reaction can be performed in the liquid phase or in the gaseous phase and the reagents can flow inside the tube with a laminar flow or with a turbulent flow, and the flow is generally continuous. The reaction temperature can lie, in particular, in the range 100° C. to 900° C., and more particularly it can lie in the range 500° C. to 850° C.

The chemical reaction can be a thermal cracking reaction performed on various organic substances, and in particular on 1,2-dichloroethane for the purpose of obtaining vinyl chloride.

The method is particularly adapted to cracking a mixture of water and hydrocarbons, i.e. to a so-called "steam cracking" reaction, as performed in a cracking tube disposed in the reaction zone of a cracking furnace. Under such circumstances, to perform the method, the cracking temperature increases along the cracking tube from its point of entry into the radiation zone of the furnace up to its point of exit therefrom, i.e. in the flow direction of the reaction mixture. In particular, the cracking temperature of the mixture of hydrocarbons and steam lies in the range 500° C. to 700° C. and preferably in the range 550° C. to 660° C. at the inlet to the radiation zone of the furnace, while at the outlet therefrom it lies in the range 800° C. to 880° C., and preferably in the range 810° C. to 860° C., with the increase in the cracking temperature along the tube being of any kind, e.g. uniform, or else as described in French patents FR-A-2 600 665 and FR-A-2 600 667. Furthermore, the mixture of hydrocarbons and steam is generally subjected to preheating prior to being admitted into the radiation zone of the furnace, said preheating being performed by any known means, in particular in a convection heating zone of the furnace. The mean transit time of the hydrocarbon and steam mixture flowing along the tube between its entry into and exit from the radiation zone generally lies in the range 300 milliseconds (ms) to 1800 ms, and preferably lies in the range 400 ms to 1400 ms. The composition of the hydrocarbon and steam mixture is such that the ratio by weight of the quantity of hydrocarbons to the quantity of steam lies in the range 1 to 10, and preferably lies in the range 2 to 6.

In the steam cracking method, it is equally possible to make use of liquid hydrocarbons or of gaseous hydrocarbons. The liquid hydrocarbons can be selected from naphtha which is made up of hydrocarbons having about 5 to 10 carbon atoms; light gasolines made up of hydrocarbons having about 5 to 6 atoms of carbon, gas oil constituted by hydrocarbons having about 8 to 15 atoms of carbon, and mixtures thereof. They can also be used in mixtures with saturated and unsaturated hydrocarbons having 3 to 6 atoms of carbon. The gaseous hydrocarbons can be alkanes having 2 to 4 atoms of carbon and/or methane and/or alkanes having 5 or 6 atoms of carbon. In particular, it is possible to perform a steam cracking method on natural gas, on liquefied petroleum gas (LPG) or on ethane which is a secondary product derived from the steam cracking of liquid hydrocarbons such as naphtha or gas oil.

The present invention also provides a device for implementing the above-described method. This device is constituted by a furnace comprising a radiation thermal enclosure fitted with heater means constituted by burners and through which at least one tube passes, the device being characterized in that it is provided with at least one excitation means suitable for generating vibration in at least a portion of the tube in order to limit the deposition on its inside wall of by-products obtained during a chemical reaction performed inside the tube.

The device of the invention may be constituted by a furnace including at least one tube disposed in its radiation thermal enclosure. The mean inside diameter of the tube generally lies in the range 20 mm to 200 mm and preferably lies in the range 30 mm to 150 mm, the tube having a wall thickness lying in the range 3 mm to 15 mm and generally being constituted by a straight segment or by a plurality of straight segments that are interconnected, in particular by bends. The furnace is adapted to the chemical reaction performed. In particular, when the method is used for performing a steam cracking reaction, the furnace must be a steam cracking furnace which comprises a radiation thermal enclosure through which at least one cracking tube passes in the form of a horizontal or vertical coil. The cracking tube generally has a ratio of length to mean inside diameter lying in the range 30 to 1500, and preferably lying in the range 300 to 1000. In particular, the mean inside diameter of the cracking tube is preferably equal to or greater than 100 mm, such that the mean transit time of the reaction mixture in the cracking tube can be relatively large and such that the head losses in the mixture flowing along the cracking tube can be small. Nevertheless, the mean inside diameter and the length of the tube should remain within ranges of values that are compatible with the thermal and mechanical constraints to which the materials constituting the cracking tube are subjected. In particular, the mean inside diameter of the cracking tube cannot exceed about 250 mm. Advantageously, the cracking tube can have an inside diameter that varies along its length as described in French patents FR-A-2 600 677 and FR-A-2 600 641. In practice, the cracking tube is disposed in the form of a coil constituted by a succession of straight line segments interconnected by bends.

The means for exciting the device of the invention can be a mechanical vibration generator disposed inside or outside the radiation zone of the furnace and connected to the tube by means of a mechanical link. The source of vibrations can be a vibrating machine.

The excitation means can alternatively be a pressure wave generator, and in particular a soundwave generator. When standing pressure waves are generated, the walls of the radiation zone serve to reflect waves. The pressure wave generator can be a vibrating membrane, such as that of a loudspeaker, a siren, or a foghorn. The excitation means can also be constituted by one or more burners, with each burner being equipped with means for generating pulses in the flow of fuel feeding it. This pulse generator means can be a periodically-operating shutter, serving to shut the fuel feed outlet and actuated by means of a vibrating pot.

BRIEF DESCRIPTION OF THE DRAWING

FIG. 1 is a longitudinal diagrammatic section through a horizontal steam cracking furnace comprising a radiation thermal enclosure 1 through which a cracking tube passes, being disposed in a serpentine form of a coil made up of eight horizontal straight segments interconnected by bends, the sections 2 to 9 having a mean inside diameter of 108 mm. The entry and the exit of the cracking tube into and from the radiation thermal enclosure are respectively referenced 10 and 11. This steam cracking furnace comprises a radiation thermal enclosure provided with heating means constituted by burners disposed in rows on the walls of the enclosure. The disposition, adjustment, and/or size of the burners inside the thermal enclosure are such that the vibrations of the flames of the burners produce a system of pressure waves inside the radiation thermal enclosure.

FIG. 2 is a diagram showing the radiation enclosure 1 of a steam cracking furnace in a cross-section containing burners. Each t)f the walls 12 and 13 is fitted with five rows of burners 14. The figure shows only one burner per row.

BRIEF DESCRIPTION OF PREFERRED EMBODIMENT

The following example illustrates the present invention.

EXAMPLE 1

Figure 1:
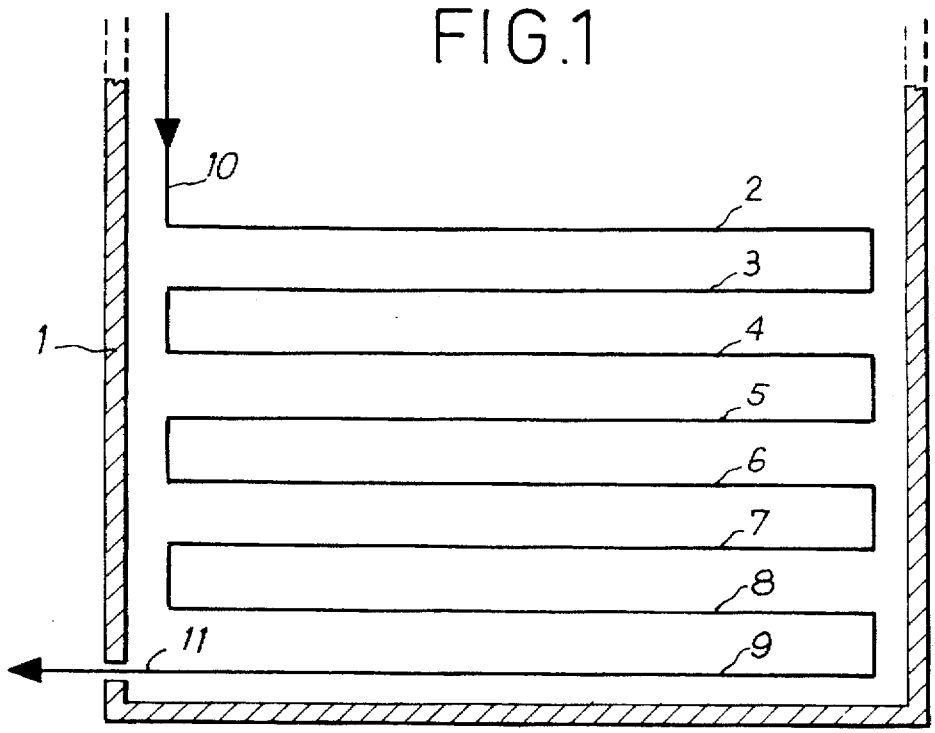
FIGS. 1 and 2 are diagrams showing two different sections of a steam cracking furnace.
Figure 2:
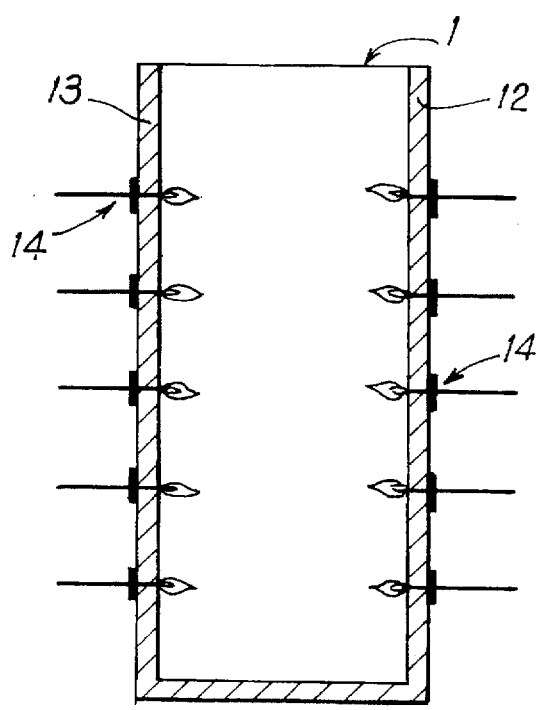

Operation takes place in a steam cracking furnace such as that shown diagrammatically in FIG. 1, which furnace conprises a radiation thermal enclosure 1 made of fire bricks, in the form of a rectangular parallelepiped having inside dimensions of 9.75 meters (m) in length, 1.70 m in width, and 4.85 m in height. A cracking tube made of refractory steel based on nickel and chromium having an inside diameter of 108 mm, and a wall thickness of 8 mm is placed inside the enclosure 1, and given the size of the enclosure and the thermal stresses of the furnace, the tube has a total length of 80 meters between its entry into the enclosure and its exit therefrom. The cracking tube is disposed in a serpentine form comprising eight equal length horizontal straight segments which are interconnected by bends. The inside diameter of the straight segments is constant and equal to 108 mm.

The radiation thermal enclosure of the steam cracking furnace is provided with burners disposed on the walls of the enclosure in five horizontal rows and situated at equal distances apart with their flames directed substantially perpendicularly toward the respective adjacent straight tube segments. The heating power of the set of burners is distributed uniformly between said five rows.

All of the burners are fed firstly at a substantially constant flow rate of 1750 kg/hour of fuel made up of a gaseous mixture comprising 90% by volume methane, and 10% by volume hydrogen, together with air preheated to 100° C. and in sufficient quantity to ensure good combustion of the gaseous mixture.

A mixture of liquid hydrocarbons and steam is caused to flow along this cracking tube. The liquid hydrocarbons are constituted by a naphtha having a relative density of 0.717, having an ASTM distillation gap of 44°/165° C., and having the following composition by weight: 32.74% linear paraffins, 30.95% branching paraffins, 28.80% cycloparaffin compounds, and 7.51% aromatic compounds. The composition of the mixture of naphtha and steam as used is such that the ratio by weight of the quantity of naphtha to the quantity of steam is four. Thus, naphtha is injected into the cracking tube at a flow rate of 3700 kg/h while steam is injected therein at a rate of 925 kg/h.

The cracking temperature of the mixture of naphtha and steam is 570° C. at the entry to the radiation zone of the furnace and rises to 810° C. at the exit therefrom. At the outlet from the furnace, the pressure of the mixture is 170 kPa. The mean transit time of the mixture of naphtha and steam flowing along the cracking tube between the entry to and the exit from the radiation zone of the furnace is 900 ms.

Under such conditions, the following quantities of various substances are produced per hour: 725 kg of ethylene; 598 kg of propylene; 102 kg of isobutene; 157 kg of butadine; and 186 kg of ethane, and the maximum skin temperature to be measured is 990° C.

For two days, the feed to the burners was modified so as to feed them with 1750 kg/hour of a new mixture of gases comprising, by volume, 75% methone and 25% hydrogen. Under the new conditions, the yield and the efficiency of the furnace were not changed and it was observed that the cracking tube vibrated due to the waves generated by the vibrations of the flames of the burners. The cracking tube is thus caused to vibrate continuously for a plurality of days. Such vibration of the cracking tube removes a fraction of the coke that has previously been deposited on its inside wall, and at the end of the two days this was manifested by new maximum skin temperatures lower than before and of the order of 950° C. In other words, periodically the composition of the fuel feeding the burners is varied so as to generate pressure waves within the furnace enclosure for imparting vibrations to the exterior of the cracking tube.

What is claimed is:

1. A method of manufacturing one or more chemical products in which a chemical reaction is performed by causing one or more reagents to flow under normally turbulent conditions inside a tube disposed in a radiation zone of a furnace so as to receive heat required for the reaction, said radiation zone containing gases, and in which heat is directed in said radiation zone toward the outside of said tube so that said tube effectively transmits heat thus directed to the inside of the tube, which comprises providing a pressure wave source spaced from the tube and directing pressure waves from said source substantially perpendicularly to the longitudinal axis of the tube so as to apply the pressure waves to the external wall of the tube, said pressure waves being sufficient that in response to said pressure waves the tube is caused to vibrate transversely of its longitudinal axis at substantially a resonant frequency of the tube as disposed in the reaction zone so as to limit the deposition of reaction by-products on the inside wall of the tube while continuing the chemical reaction within the tube.

2. A method according to claim 1, wherein the tube is thus vibrated at a frequency up to 1000 Hz.

3. A method according to claim 1, wherein the chemical reaction is a thermal cracking reaction of dicholoro-1, 2 ethane.

4. A method according claim 1, wherein the chemical reaction is a cracking reaction performed on a mixture of hydrocarbons and steam.

5. A method according to claim 1, wherein the pressure wave is caused by the vibration of flames of burners disposed in the walls of the radiation zone, said flames being directed substantially perpendicularly toward the longitudinal axis of the tube.

6. A method according to claim 5, wherein the composition of the fuel feeding the burners is chosen to cause the vibration of the flames.

7. A method according to claim 1, wherein the pressure wave source is a sound wave generator.

8. A method according to claim 5, wherein the burners are equipped with means for generating pulses in the flow of the fuel feeding the burners.

9. A method according to claim 8, wherein the means for generating pulses is a periodically operating shut-off valve serving to shut a fuel feed outlet for supplying the fuel to the burners.

10. A method according to claim 1, wherein the reaction temperature of the chemical reaction is in the range of 100° to 900° C.

11. A method according to claim 4, wherein the temperature of the cracking reaction lies in the range of 500° C. to 700° C. at an inlet to the radiation zone and in the range of 800° C. to 880° C. at an outlet to the radiation zone.

12. A method according to claim 1, wherein the tube is thus vibrated at a frequency up to 1,000 Hz.

13. A method of manufacturing one or more chemical products in which a chemical reaction is performed by causing one or more reagents to flow under normally turbulent conditions inside a tube disposed in a radiation zone of a furnace so as to receive heat required for the reaction, and in which heat is directed in said radiation zone toward the outside of said tube so that said tube effectively transmits heat thus directed to the inside of the tube, which comprises applying vibrations to the external wall of the tube by a mechanical vibration source connected to the tube by means of a mechanical link so that the tube is thus vibrated transversely of its longitudinal axis at substantially a resonant frequency of the tube as disposed in the reaction zone so as to limit the deposition of reaction by-products on the inside wall of the tube while continuing the chemical reaction within the tube.

14. A method according to claim 13, wherein the mechanical vibration source is disposed outside the radiation zone of the furnace.

15. A method according to claim 1, wherein the pressure wave source is a vibrating membrane.

16. A method according to claim 1, wherein the pressure wave source is a loudspeaker, a siren or a foghorn.

17. A method according to claim 13, wherein the chemical reaction is a thermal cracking reaction of 1,2-dichloroethane.

18. A method according to claim 13, wherein the chemical reaction is a cracking reaction performed on a mixture of hydrocarbons and steam.

19. A method according to claim 13, wherein the reaction temperature is in the range of 100° to 900° C.

20. A method according to claim 18, wherein the cracking temperature lies in the range of 500° C. to 700° C. at an inlet to the radiation zone and in the range of 800° C. to 880° C. at an outlet to the radiation zone.

21. A method of manufacturing one or more chemical products in which a chemical reaction is performed by causing one or more reagents to flow under normally turbulent conditions inside a tube disposed in a radiation zone of a furnace, and in which heat is directed in said radiation zone toward the outside of said tube so as to receive heat required for the reaction, which comprises providing a vibration source spaced from the tube and vibrating the tube so as to cause it to vibrate transversely of its longitudinal axis at substantially a resonant frequency of said tube as disposed in the reaction zone, at least one point of the tube thus vibrating with an amplitude greater than $10^{-4}$ times the inside diameter of the tube so as to limit the deposition of reaction by-products on the inside wall of the tube and continuing the chemical reaction within the tube.

22. A method according to claim 21, wherein the chemical reaction is a thermal cracking reaction of 1,2-dichloroethane.

23. A method according to claim 21, wherein the chemical reaction is a cracking reaction performed on a mixture of hydrocarbons and steam.

24. A method according to claim 1, wherein at least one point of the tube is vibrated transversely of its longitudinal axis greater than $10^{-4}$ times the inside diameter of the tube.

25. A method according to claim 13, wherein at least one point of the tube is vibrated transversely of its longitudinal axis greater than $10^{-4}$ times the inside diameter of the tube.

26. A method according to claim 13, in which the hydrocarbons are selected from the group consisting of naphthas, mixtures of naphthas with saturated or unsaturated hydrocarbons having 3 to 6 carbon atoms, or gaseous hydrocarbons which are alkanes having from 1 to 6 carbon atoms.

27. A method according to claim 18, in which the hydrocarbons are selected from the group consisting of naphthas, mixtures of naphthas with saturated or unsaturated hydrocarbons having 3 to 6 carbon atoms, or gaseous hydrocarbons which are alkanes having from 1 to 6 carbon atoms.

28. A process according to claim 1, wherein to limit deposit of the by-products on the inside wall of the tube the tube is caused to vibrate continuously for a plurality of days.

* * * * *